United States Patent

Schülze et al.

Patent Number: 4,637,828
Date of Patent: Jan. 20, 1987

[54] PLANT GROWTH REGULATORS

[75] Inventors: Ernst-Friedrich Schülze, Hofheim am Taunus; Helmut Bürstell, Frankfurt am Main; Erwin Hacker, Hocheim am Main, all of Fed. Rep. of Germany

[73] Assignee: Hoechst Aktiengesellschaft, Frankfurt, Fed. Rep. of Germany

[21] Appl. No.: 740,286

[22] Filed: Jun. 3, 1985

[30] Foreign Application Priority Data

Jun. 5, 1984 [DE]  Fed. Rep. of Germany ....... 3420832

[51] Int. Cl.$^4$ ................ A01N 43/50; A01N 33/12
[52] U.S. Cl. ........................... 71/76; 71/92; 71/121
[58] Field of Search ............... 71/76, 77, 78, 92, 121

[56] References Cited

U.S. PATENT DOCUMENTS 4,182,621  1/1980  Ogata et al. .......................... 71/76
4,488,901  12/1984  Farkas et al. ........................ 71/121

FOREIGN PATENT DOCUMENTS 3217094  10/1983  Fed. Rep. of Germany .......... 71/92

OTHER PUBLICATIONS

The Agrochemicals Handbook (Agrochem), Royal Society of Chemistry, 1983, United Kingdom.
Phad et al, "Effect of Different Growth, etc." (1980) CA 93:232605z (1980).
Kuehn et al, "Plant Growth-Regulating, etc.," (1976) CA 86:51577b (1977).

*Primary Examiner*—Glennon H. Hollrah
*Assistant Examiner*—Robert Lelkes
*Attorney, Agent, or Firm*—Curtis, Morris & Safford

[57] ABSTRACT

Plant growth regulators comprising a compound of the formula I

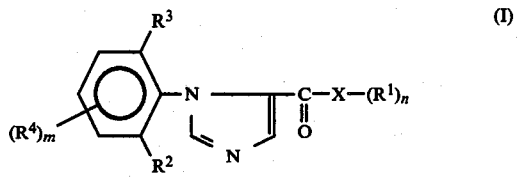

wherein x=0, S or N, $R^1$=hydrogen, phenyl, alkenyl or (substituted) alkyl and, when X=0 or S, also a metal cation or ammonium cation, n=1 when X=0 or S, and 1 or 2 when X=N, $R^2$ and $R^3$=alkyl, $R^4$=alkyl, alkoxy or halogen and m=0, 1, 2 or 3, and, when $R^1$ does not represent a cation, their acid addition salts, complex salts or quaternization products, in combination with a compound of the formula II

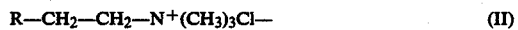

wherein R denotes OH or Cl, or in combination with N,N-dimethylpiperidinium chloride.

9 Claims, No Drawings

PLANT GROWTH REGULATORS

The present invention relates to plant growth regulators which contain a compound of the formula I

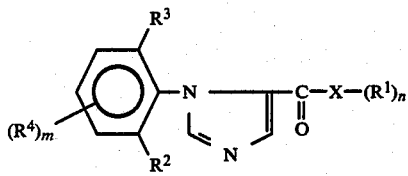

wherein X denotes O, S or N, $R^1$ denotes hydrogen, phenyl, ($C_2$-$C_6$)-alkenyl or ($C_1$-$C_6$)-alkyl which can be monosubstituted to trisubstituted by ($C_1$-$C_6$)-alkoxy, ($C_1$-$C_3$)-dialkylamino or halogen, and, when X=O or S, may furthermore denote a metal cation or an ammonium cation, n can denote 1 when X=O or S, and 1 or 2 when X=N, the radicals $R^1$ being identical or different when n=2, $R^2$ and $R^3$ independently of one another denote ($C_1$-$C_4$)-alkyl, $R^4$ is identical or different and denotes ($C_1$-$C_4$)-alkyl, ($C_1$-$C_4$)-alkoxy or halogen, and m denotes the number 0, 1, 2 or 3, and, in the case in which $R^1$ does not represent a cation, their acid addition salts, complex salts or quaternization products, in combination with a compound of the formula II

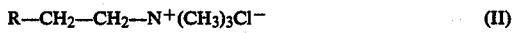

wherein R denotes OH or Cl, or with a compound of the formula II

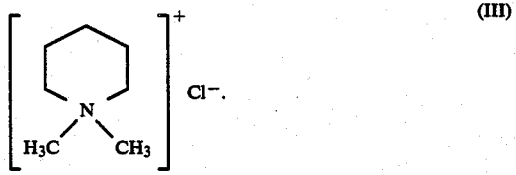

Particularly suitable metal cations for the compounds of the formula I when X=O or S are alkali metal and alkaline earth metal cations, such as Na, K, Mg or Ca ions.

Among the acid addition salts, complex salts and quaternization products of the compounds of the formula I, those which may be mentioned are the salts of organic and inorganic acids, such as benzoates, fumarates, oxalates, phenolates, sulfonates, nitrates, chlorides, bromides and sulfates, complexes with metals of Groups Ib, IIb, Ivb or VIII of the periodic table, for example copper, zinc and tin, and quaternization products with alkyl, in particular ($C_1$-$C_6$)-alkyl, and phenacyl halides which are optionally substituted in the phenyl radical, in particular halogenated phenacyl halides.

The compounds of the formula I and their salts, complex salts and quaternization products, and the plant growth-regulating action of these, are disclosed in German Offenlegungsschrift No. 32 17 094.7. The following compounds (1–13) of the formula I in which m=0 may be mentioned as examples:

TABLE 1

| Compound | X-($R^1$)$_n$ | $R^2$ | $R^3$ |
|---|---|---|---|
| 1 | O—$CH_3$ | $C_2H_5$ | $C_2H_5$ |
| 2 | O—CH($CH_3$)$_2$ | " | " |
| 3 | O—n-$C_8H_{17}$ | " | " |
| 4 | O—Na | " | " |
| 5 | OH | " | " |
| 6 | OH.hydrochloride | " | " |
| 7 | $NH_2$ | " | " |
| 8 | NH—CH—($CH_3$)$_2$ | " | " |
| 9 | $SC_2H_5$ | " | " |
| 10 | O—[$H_4$N] | " | " |
| 11 | O—K | " | " |
| 12 | O.½ Mg | " | " |
| 13 | OH | $CH_3$ | " |

The compounds of the formulae II and III are known commercial products. The compound of the formula II in which R=Cl (compound IIa, chloroethyltrimethylamonnium chloride) has the common name chlormequate chloride or CCC.

The compound of the formula III (1,1-dimethylpiperidinium chloride) is known by the name mepiquate chloride. The growth-regulating actions of the compounds of the formulae II and III are described in Plant Growth Regulator Handbook of the Plant Growth Regulator Working Group, 2nd edition, 1981.

Instead of the compounds of the formulae II and III, it is also possible in principle to use analogous salts which, instead of the chloride, contain another anion which can be used in agriculture, such as, for example, bromide, nitrate or ½ sulfate.

Surprisingly, striking synergistic effects are found when the compounds of the formula I are combined with the compounds of the formula II or III. Thus, the desired effects can be achieved using the combinations according to the invention in substantially smaller doses than would be expected from the action of the individual components. Examples of the effects are the following: increasing the firmness of crops, for example cereals, corn, rice, soybean, millet, rape and cotton, inhibiting the growth of lawns, influencing plant constituents, such as carbohydrates and proteins, increasing the yield and improving the leaf fall and shedding of fruit, in particular in the case of citrus fruits, or reducing the retaining force. The combinations according to the invention, can also be used for reducing wild growth, so that the combinations can also be employed in conservation.

Furthermore, the agents according to the invention are outstandingly suitable for the general control and inhibition of undesired vegetative growth, such as the formation of sideshoots, without destroying the plants.

The compounds of the formula I can also advantageously be combined with two different compounds of the formula II or III, for example a compound of the formula I with two compounds of the formula II.

The mixing ratios of the components of the formula I to the compounds of the formulae II or III can vary within wide limits, for example between 250:1 and 1:10. The choice of the mixing ratio depends on the type of components in the mixture, on the stage of development of the plants and on the desired degree of growth-regulating activity. Preferably, mixing ratios of from 10:1 to 1:10 are chosen; especially preferred ratios are between 1:1 to 1:10.

The application rate of the compounds of the formula I in the mixtures of active ingredients is in general between 0.05 and 2.5 kg/ha, while the application rates of the compounds of the formulae II and III vary between 0.01 and 5 kg/ha.

The total application rate of the mixture is, in particular, from 0.25 to 1.25 kg/ha for the combination I+II, and, in particular, between 0.25 and 2.5 kg/ha in the case of the combination I+III.

The agents according to the invention can either be formulations consisting of mixtures of the components (wettable powders or emulsion concentrates), which are then brought to use after dilution with water in a conventional manner, or be prepared in the form of so-called tank mixtures by diluting the separately formulated components with water.

The agents according to the invention can be offered commercially in the conventional formulations familiar to the skilled worker, for example as wettable powders, emulsifiable concentrates or atomizable solutions. The formulated agents contain the combinations of active ingredients in general in a range from 2 to 95% by weight, in addition to conventional formulation auxiliaries.

Wettable powders are preparations which can be dispersed homogeneously in water and which, in addition to the active ingredients and a diluent or inert substance, contain wetting agents, for example polyoxyethylated alkylphenols, polyoxyethylated oleylamines or stearylamines or polyoxyethylated fatty alcohols, alkylsulfonates or alkylphenylsulfonates, and dispersants, for example sodium ligninsulfonate, sodium dinaphthylmethanedisulfonate, sodium dibutylnaphthalenesulfonate or sodium oleylmethyltaurate.

Emulsifiable concentrates are obtained by dissolving the mixture of active ingredients in an organic solvent, for example butanol, cyclohexanone, dimethylformamide, xylene or relatively high-boiling aromatics, and adding a nonionic wetting agent, for example a polyethylated alkylphenol or a polyoxyethylated oleylamine or stearylamine.

In the case of growth regulators, the concentrations of the active ingredients in the commercial formulations can vary. In wettable powders, the concentration of active ingredients varies between, for example, about 10% and 95%, the remainder consisting of the above-mentioned formulation additives. In the case of emulsifiable concentrates, the concentration of active ingredients is about 10% to 80%. Dust-like formulations generally contain 5% to 20% of active ingredient, while atomizable solutions contain about 2% to 20%. In the case of granules, the content of active ingredients is partly dependent on the form (liquid or solid) in which the active ingredients are present and on the granulation assistants, fillers, etc. used.

For use, the commercial concentrates are, if necessary, diluted in a conventional manner, for example with water in the case of wettable powders and emulsifiable concentrates. Dust-like and granulated formulations and atomizable solutions are not diluted with any further inert substances before use. The required application rate varies with the external conditions, such as temperature, moisture, etc.

The agents according to the invention can be further combined with herbicides, fungicides or insecticides and other growth regulators.

Furthermore, in addition to being combined with the compounds of the formulae II and III, the compounds of the formula I can also advantageously be combined with the following growth regulators: ancymidol ($\alpha$-cyclopropyl-4-methoxy-$\alpha$-(pyrimidin-5-yl)-benzyl alcohol, tetcyclacis (3a$\alpha$,4$\beta$,4a$\alpha$,6a$\alpha$, 7$\beta$,7a$\alpha$)-1-(4-chlorophenyl)-3a,4,4a,6a,7,7a-hexahydro-4,7-methano-1H-[1,2]diazeto|3,4f|benzotriazole), daminozide (succinic acid mono(2,2-dimethylhydrazide), mefluidide (5'-trifluoromethanesulfonamido)-acet-2',4'-xylidide), maleic hydrazide ("MH", 1,2-dihydro-3,6-pyridazinedione) and chlorflurenol (2-chloro-9-hydroxy-9H-fluorene-9-carboxylic acid).

These compounds are described in The Pesticide Manual, 7th edition, British Corp. Protection Council, 1983. The compounds of the formula I can also be combined with natural or synthetic plant hormones, for example with auxines, such as $\alpha$-naphthylacetic acid or indole-3-acetic acid, or with cytokinins.

A. FORMULATION EXAMPLES

Example I

An aqueous solution of a combination according to the invention is obtained from 20.0% by weight of technical-grade active ingredient of the formula I in which $X=O$, $R^1=Na$ and $n=1$, 10.0% by weight of active ingredient of the formula II in which $R=OH$, 8.0% by weight of dimethylformamide, 10.0% by weight of sodium laurylsulfate, 5.0% by weight of isopropanol and 47.0% by weight of tap water.

The components of the formula I and II are dissolved with stirring and gentle heating at 40° to 50° C., after which the emulsifier is added. Stirring is continued for 20 minutes at 40° to 50° C., until the solution is clear and free from streaks.

Example II

An aqueous solution of a combination is obtained from 22.0% by weight of technical-grade active ingredient of the formula I in which $X=O$, $R^1=NH_4$ and $n=1$, 8.0% by weight of active ingredient of the formula III, 10.0% by weight of ethylene glycol monomethyl ether, 10.0% by weight of oxyethylated nonylphenol (10 EO) and (50.0% by weight of tap water.

The components are dissolved as stated in Example 1, at 40°–50° C., and stirring is continued for about 20 minutes.

Example III

A wettable powder which is readily dispersible in water is obtained from

20% by weight of technical-grade active ingredient of the formula I in which $X=O$, $R^1=Na$ and $n=1$, 20% by weight of active ingredient of the formula I ($R=Cl$), 45% by weight of basic aluminum silicate (kaolinite), 8% by weight of potassium ligninsulfonate and 7% by weight of sodium oleylmethyltaurate.

The components are mixed thoroughly in a drum mixer and then milled in a pinned-disk mill once at 3,000 rpm. The finished mill base is again mixed, and is milled once at 1,200 rpm.

B. BIOLOGICAL EXAMPLES

The action of the combinations according to the invention on various cereal species was investigated in the open in tests on small plots.

The agents according to the invention were applied by the post-emergence method at various stages of development of the plants, on 10 m² test plots, the volume of water used being 400 liters/ha. Each trial was repeated four times. The plants were rated at 14-day intervals after application, phytotoxicity, height of growth and development being investigated. The results are shown in Table I below.

The results from Table I confirm the outstanding synergistic effects obtained with the combinations according to the invention. The effect observed (shortening of stems) is substantially greater than the effect which would be expected from the action of the individual components. This synergistic effect occurred over a wide range of plant development.

TABLE I

| Compound/combination | Application rate kg of a.i./ha | Inhibition of growth in % for wheat | barley | rye | oats | Phytotoxicity |
|---|---|---|---|---|---|---|
| IIa | 0.6 | 8 | 0 | 3 | 3 | no damage |
| III | 0.9 | 0 | 8 | 5 | 0 | no damage |
| 1 | 0.6 | 7 | 7 | 5 | 6 | no damage |
| 1 + IIa | 0.6 + 0.6 | 12 | 22 | 13 | 10 | no damage |
| 1 + III | 0.6 + 0.9 | 14 | 20 | 11 | 11 | no damage |
| 2 | 0.6 | 8 | 7 | 6 | 5 | no damage |
| 2 + IIa | 0.6 + 0.6 | 18 | 27 | 14 | 14 | no damage |
| 2 + III | 0.6 + 0.9 | 15 | 24 | 14 | 11 | no damage |
| 5 | 0.06 | 0 | 0 | 0 | 0 | no damage |
|  | 0.6 | 8 | 8 | 6 | 6 | no damage |
| 5 + IIa | 0.06 + 0.6 | 18 | 24 | — | 13 | no damage |
| 5 + IIa | 0.6 + 0.6 | 20 | 28 | 15 | 15 | no damage |
| 5 + III | 0.6 + 0.9 | 15 | 24 | 15 | 12 | no damage |
| 9 | 0.6 | 8 | 9 | 7 | 5 | no damage |
| 9 + IIa | 0.6 + 0.6 | 15 | 25 | 14 | 14 | no damage |
| 9 + III | 0.6 + 0.9 | 13 | 23 | 12 | 11 | no damage |
| 10 | 0.6 | 8 | 8 | 6 | 6 | no damage |
| 10 + IIa | 0.6 + 0.6 | 15 | 28 | 15 | 14 | no damage |
| 10 + III | 0.6 + 0.9 | 16 | 25 | 12 | 12 | no damage |
| 12 | 0.6 | 6 | 7 | 4 | 5 | no damage |
| 12 + IIa | 0.6 + 0.6 | 17 | 18 | 14 | 15 | no damage |
| 12 + III | 0.6 + 0.9 | 13 | 20 | 14 | 10 | no damage |
| 11 | 0.06 | 0 | 0 | 0 | 0 | no damage |
|  | 0.6 | 4 | 5 | 2 | 2 | no damage |
| 11 + IIa | 0.06 + 0.6 | 12 | 13 | — | 10 | no damage |
| 11 + IIa | 0.6 + 0.6 | 14 | 15 | 10 | 12 | no damage |
| 11 + III | 0.6 + 0.9 | 10 | 17 | 12 | 11 | no damage | a.i. = active ingredient; Plot size: 10 m²; Amount of water used: 400 liters/ha
Stage of application: end of tillering, beginning of shooting
Rating: 4 weeks after application
For compounds 1, 2, 5, 9, 10, 11 and 12, see pages 2 and 3; Compounds IIa and III, see page 3

We claim:

1. A plant growth regulator consisting essentially of a compound (I)

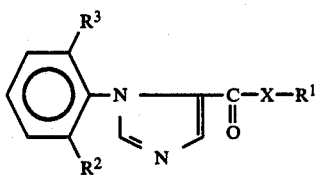

wherein X is O or S; R' is hydrogen, $(C_1-C_6)$-alkyl, a metal cation, or an ammonium cation; $R^2$ and $R^3$ are the same or different $(C_1-C_4)$-alkyl, or when $R^1$ is not a cation, (I) is an acid addition salt, a complex salt, or a quaternization product of such a compound, in combination with a synergistically effective amount of compound (II) of the formula

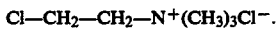

$$Cl-CH_2-CH_2-N^+(CH_3)_3Cl^-.$$

2. A plant growth regulator as in claim 1 wherein $R^1$ is Na, K, Mg, or Ca.

3. A plant growth regulator as in claim 1 wherein said compound (I) or an acid addition salt, complex salt, or quaternization product thereof and compound (II) are present in combination in a weight ratio from 1:1 to 1:10.

4. A plant growth regulator as in claim 1 wherein $R^2$ and $R^3$ are ethyl, X is O, and $R^1$ is hydrogen.

5. A plant growth regulator as in claim 1 wherein $R^2$ and $R^3$ are ethyl, X is O, and $R^1$ is Na, K or Mg.

6. A plant growth regulator as in claim 1 wherein $R^2$ and $R^3$ are ethyl, X is O, and $R^1$ is $(C_1-C_3)$-alkyl.

7. A plant growth regulator as in claim 1 wherein $R^2$ and $R^3$ are each ethyl, and $-X-R^1$ is $-OK$.

8. A method for regulating plant growth in a cultivated area which comprises applying an effective amount of a plant growth regulator as in claim 1 to said plant growth or to the cultivated area.

9. A method as in claim 8 wherein said plant growth is inhibited.

* * * * *